United States Patent [19]

Rhomberg et al.

[11] 4,034,096
[45] July 5, 1977

[54] NITROGEN CONTAINING DERIVATIVES OF CYCLOPENTENO-QUINOLONE COMPOUNDS AND BACTERIOSTATIC COMPOSITIONS

[75] Inventors: Alfred Rhomberg, Mannheim-Neuostheim; Herbert Berger, Mannheim-Kafertal, both of Germany; Kurt Stach, deceased, late of Mannheim-Waldhof, Germany; by Werner Plattner, administrator, Linz, Austria; Wolfgang Vömel, Mannheim; Winfriede Sauer, Mannheim-Wallstadt, both of Germany

[73] Assignee: Boehringer Mannheim G.m.b.H., Mannheim-Waldhof, Germany

[22] Filed: July 14, 1975

[21] Appl. No.: 595,953

Related U.S. Application Data

[62] Division of Ser. No. 515,790, Oct. 17, 1974.

[30] Foreign Application Priority Data

Nov. 27, 1973  Germany ..................... 2358909

[52] U.S. Cl. ..................... 424/258; 260/287 CF
[51] Int. Cl.² ..................... C07D 215/56
[58] Field of Search ............. 260/287 CF; 424/258

[56] References Cited
UNITED STATES PATENTS 3,324,003  6/1967  Lesher .................... 424/258

FOREIGN PATENTS OR APPLICATIONS 1,912,944  10/1970  Germany ................... 260/287

*Primary Examiner*—Donald G. Daus
*Assistant Examiner*—David E. Wheeler
*Attorney, Agent, or Firm*—Burgess, Dinklage & Sprung

[57] ABSTRACT

New cyclopenteno-quinolone derivatives of the formula

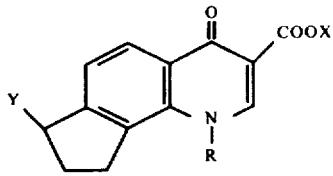

wherein
R is a saturated or unsaturated aliphatic hydrocarbyl, e.g., alkyl and alkenyl,
X is hydrogen or alkyl, and
Y is halogen, azido, alkylthio, alkyl-sulfonyl, or nitrile or unsubstituted or substituted (e.g., alkyl mono or di-substituted) amino;

and the pharmacologically compatible salts thereof; are outstandingly effective as bacteriostats in mammals.

17 Claims, No Drawings

NITROGEN CONTAINING DERIVATIVES OF CYCLOPENTENO-QUINOLONE COMPOUNDS AND BACTERIOSTATIC COMPOSITIONS

This is a division of application Ser. No. 515,790 filed Oct. 17, 1974.

The present invention is concerned with new cyclopenteno-quinolone derivatives and therapeutic compositions and uses thereof.

The new cyclopenteno-quinolone derivatives according to the present invention are compounds of the general formula:

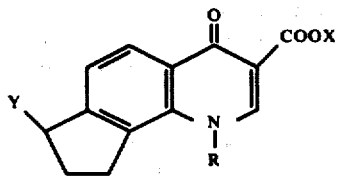

(I)

wherein
R is a saturated or unsaturated aliphatic hydrocarbyl, e.g. alkyl and alkenyl,
X is hydrogen or alkyl, and
Y is halogen, axido, alkylthio, alkyl-sulfonyl, or nitrile or unsubstituted or substituted (e.g. alkyl mono or di-substituted) amino;
and the pharmacologically compatible salts thereof.

The amino group Y in the above-given general formula (I) can be not only a free amino group but also a mono- or dialkylamino, mono- or diacylamino, mono- or dialkylamino-methyleneamino, pyrrolidino or piperidino radical.

The aliphatic radicals R and the alkyl radicals X and Y can contain up to 5 and preferably up to 3 carbon atoms.

The new compounds according to the present invention differ from the structurally similar compounds described in German Patent Specification No. 1,770,951 by having a substituent in the cyclopentene ring.

Surprisingly, the new compounds according to the present invention, in comparison with the known compounds, have about the same anti-microbial action in vitro but a substantially stronger action in vivo, especially in the urinary tract.

The new compounds according to the present invention can be prepared, for example, by reacting a compound of the general formula:

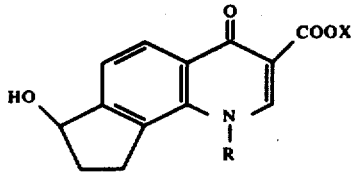

(II)

wherein R and X have the same meanings as above, with a conventional halogenation agent, whereafter in the halogen compound thus obtained, if desired, the halogen atom is exchanged in conventional manner by another substituent Y and/or converted into a pharmacologically compatible salt.

The starting materials of general formula (II) are described in German Patent Specification No. 2,222,833 and can be prepared by the processes described therein.

The halogenation reaction according to the present invention can be carried out in conventional manner, preferably with the use of concentrated hydrohalic acids, for example concentrated hydrochloric acid in the presence of a zinc salt, for example zinc chloride. The halogen compound formed can then be converted by known processes into an azido group, for example with sodium azide in a solvent such as dimethyl sulphoxide, into an alkylthio radical, for example by reaction with an alkyl mercaptide in dimethyl sulphoxide, into an alkylsulphonyl radical, such as a methylsulphonyl radical, for example by reaction with sodium sulphinate in dimethyl sulphoxide, or into a nitrile group, for example by reaction with sodium cyanide or potassium cyanide. The azido group can be converted in known manner into an amino group, for example by catalytic reduction, which can then, if desired, be alkylated, acylated, condensed with aldehydes to give Schiff bases or reacted to given amidines. Alkylthio radicals can be oxidized in knonw manner to give the corresponding sulphoxides or sulphones, for example with aqueous hydrogen peroxide solution or with m-chloroperbenzoic acid.

Apart from the compounds set out in the following examples, the following compounds are also preferred according to the present invention: 1-ethyl-3-carboxy-1,4-dihydro-7-methylamino-cyclopenteno-[1,2-h] quinol-4-one; 1-ethyl-3-carboxy-1,4-dihydro-7-dimethylamino-cyclopenteno-[1,2-h] quinol-4-one; 1-ethyl-3-carboxy-1,4-dihydro-7-piperidino-cyclopenteno [1,2-h] quinol-4-one; 1-ethyl-3-carboxy-1,4-dihydro-7-(dimethylaminomethyleneamino)-cyclopenteno [1,2-h] quinol-4-one; and 1-ethyl-3-carboxyl-1,4-dihydro-7-cyanocyclopenteno [1,2-h] quinol-4-one.

The conversion of the compounds of general formula (I), in which X is a hydrogen atom, into pharmacologically compatible salts can be carried out in conventional manner, for example by neutralization with a non-toxic inorganic mase or with a non-toxic amino. Compounds of general formula (I) in which Y is an amino group can be neutralized correspondingly with non-toxic inorganic or organic acids.

The following Examples are given for the purpose of illustrating, without limitation, the present invention:

EXAMPLE 1

Preparation of 1-Ethyl-3-carboxy-7-chloro-1,4-dihydrocyclopenteno [1,2-h] quinol-4-one.

5.2 g. 1-ethyl-3-carboxy-1,4-dihydro-7-hydroxycyclopenteno [1,2-h] quinol-4-one were stirred at ambient temperature for 3 hours in a mixture of 10.4 ml. concentrated hydrochloric acid and 8.2 g. anhydrous zinc chloride. The reaction mixture was poured into ice water and the resultant precipitate was filtered off with suction and stirred three times with 40 ml. amounts of methylene chloride. The combined methylene chloride phases were dried and evaporated to dryness. There were obtained 3.1 g 1-ethyl-3-carboxy-7-chloro-1,4-dihydrocyclopenteno-[1,2-h] quinol-4-one which had a melting point of 244° – 248° C.

EXAMPLE 2

Preparation of
1-Ethyl-7-azido-3-carboxy-1,4-dihydrocyclopenteno
[1,2-h] quinol-4-one.

2.82 g. sodium azide were stirred for 20 minutes at 200° C. in 14 ml. dimethyl sulphoxide, whereby the greater part of the sodium azide was dissolved. The solution was subsequently cooled to 65° C. and then 2.82 g. 1-ethyl-3-carboxy-7-chloro-1,4dihydrocyclopenteno [1,2-h] quinol-4-one were immediately introduced therein spatula-wise so that the sodium azide did not precipitate out again, whereafter the reaction mixture was further stirred for 1 hour at 60° – 65° C. Subsequently, 68 ml. water were added thereto and the reaction mixture was cooled and filtered with suction. There were obtained 2.8 g. crude 1-ethyl-7azido-3-carboxy-1,4-dihydro-cyclopenteno [1,2-h] quinol-4-one, which was recrystallized from about 20 ml. dimethyl formamide. The yield was then 2.05 g. and the product melted at 221° – 222° C.

EXAMPLE 3

Preparation of
1-Ethyl-7-amino-3-carboxy-1,4-dihydro-cyclopenteno
[1,2-h] quinol-4-one.

0.54 g. 1-ethyl-7-azido-3-carboxy-1,4-dihydrocyclopenteno [1,2-h] quinol-4-one were dissolved in 1.7 ml. water and 1.09 ml. 2N aqueous sodium hydroxide solution and hydrogenated with hydrogen in the presence of Raney nickel at normal temperature and pressure. The reaction mixture was then purified twice with active charcoal, acidified with glacial acetic acid to pH 4 – 5 and evaporated. The residue was taken up in a little water and the finely crystalline undissolved product was separated off by centrifuging. It was thereafter slurried with water three times and decanted off. Finally, there were obtained 0.12 g. 1-ethyl-7-amino-3-carboxy-1,4-dihydro-cyclopento [1,2-h] quinol-4-one, which decomposed at 246° – 250° C.

EXAMPLE 4

Preparation of
1-Ethyl-7-acetylamino-3-carboxy-1,4-dihydro-cyclopenteno [1,2-h] quinol-4-one.

0.5 g. 1-ethyl-7-amino-3-carboxy-1,4-dihydrocyclopenteno [1,2-h] quinol-4-one were heated under reflux for 20 hours with 10 ml. acetic anhydride. After cooling, the reaction mixture was evaporated and the evaporation residue (0.55 g.) boiled for a few minutes with dimethyl formamide. There were obtained 0.25 g. 1-ethyl-7-acetylamino-3-carboxy-1,4-dihydro-cyclopentento [1,2-h] quinol-4-one, which decomposed at 292° – 303° C.

The same compound was also obtained when the solution acidified with glacial acetic acid in Example 3 was not worked up immediately but was left to stand for a comparatively long time (for example 3 weeks) at ambient temperature and then worked up in a manner analogous to that described in Example 3.

EXAMPLE 5

Preparation of
1-Ethyl-3-carboxy-1,4-dihydro-7-methylsulphonyl-cyclopenteno [1,2-h] quinol-4-one.

1.45 g. 1-ethyl-3-carboxy-7-chloro-1,4-dihydrocyclopenteno [1,2-h] quinol-4-one were dissolved in 25 ml. dimethyl sulphoxide and 2.55 g. sodium methyl sulphinate were added thereto portionwise at ambient temperature over the course of 30 minutes. The reaction mixture was further stirred for 3 hours at ambient temperature, subsequently poured into 300 ml. water, left to stand for some time at about 5° C. and then filtered off with suction. There was obtained 1.4 g. 1-ethyl-3-carboxy-1,4-dihydro-7-methyl-sulphonyl-cyclopenteno [1,2-h] quinol-4-one, which decomposed at 238° – 240° C.

EXAMPLE 6

Preparation of
1-Ethyl-3-carboxy-1,4-dihydro-7-methylthio-cyclopento [1,2-h] quinol-4-one.

100 mg. 1-ethyl-3-carboxy-7-chloro-1,4-dihydrocyclopenteno [1,2-h] quinol-4-one were dissolved in 1.5 ml. dimethyl sulphoxide and 240 mg. sodium methyl mercaptide were added portionwise at ambient temperature within the course of 5 minutes. The reaction mixture was further stirred for 2 hours at ambient temperature and the product was then precipitated out with semi-concentrated hydrochloric acid. There were obtained 35 mg. 1-ethyl-3-carboxy-1,4-dihydro-7-methylthio-cyclopenteno [1,2-h] quinol-4-one, which had a melting point of 106° – 112° C.

The present invention also provides pharmaceutical, particularly bacteriostatic, compositions containing at least one of the new compounds of general formula (I) and/or at least one pharmacologically compatible salt thereof, in admixture with a solid or liquid pharmaceutical diluent or carrier.

The bacteriostatic activity of the instant compounds was measured by determining the absolute bacteriostatic minimum concentration against a number of representative species (see Table 1) and by measuring the excretion of the test compounds in urine and the bacteriostatic effectiveness of the urine after oral administration to rats (see Table 2).

The results are set out in the following Tables.

TABLE 1

| | | Absolute Bacteriostatic Minimum Concentrations in µg/ml | | |
| --- | --- | --- | --- | --- |
| | | BACTERIUM GROUP | | |
| Test Substance | [Prep. Ex. No.] | Staphylococcus aureus (103) | Escherichia coli (108) | Proteus mirabilis (298) |
| 1-Ethyl-3-carboxy-7-azido-1,4-dihydro-cyclopenteno[1,2-h]-quinolone(4) | [2] | 4 | 0.25 | 0.25 |
| 1-Ethyl-3-carboxy-7-chloro-1,4-dihydro-cyclopenteno[1,2-h]-quinolone(4) | [1] | 32 | 1 | 2 |
| 1-Ethyl-3-carboxy-1,4-dihydro-7-methyl-sulfonyl-cyclopenteno[1,2-h]-quinolone-(4) | [5] | 8 | 1 | 1 |

TABLE 1-continued

Absolute Bacteriostatic Minimum Concentrations in µg/ml

| Test Substance | [Prep. Ex. No.] | BACTERIUM GROUP | | |
| --- | --- | --- | --- | --- |
| | | Staphylococcus aureus (103) | Escherichia coli (108) | Proteus mirabilis (298) |
| Nalidixic acid (Nogram-Winthrop) | | 32 | 1 | 2 |

TABLE 2

BACTERIOSTATIC ACTIVITY OF THE URINE OF RATS FOLLOWING ORAL ADMINISTRATION

Bacteriostatic maximum dilution of urine against Escherichia coli (106) determined in 50 ml (75 ml) urine samples 22 hours after 20 mg test compound per kg body weight had been orally administered. 6 (9) rats were employed for each experiment and every value recorded in the Table represents the results of each experiment.

| Test Compound | Prep. Ex. No. | Max. Dilution |
| --- | --- | --- |
| 1-Ethyl-3-carboxy-7-azido-1,4-dihydro-cyclopenteno[1,2-h]-quinolone-(4) | [2] | 1:1440 |
| 1-Ethyl-3-carboxy-7-chloro-1,4-dihydro-cyclopenteno[1,2-h]-quinolone-(4) | [1] | 1:1200 |
| 1-Ethyl-3-carboxy-1,4-dihydro-7-methylsulfonyl-cyclopenteno[1,2-h]-quinolone-(4) | [5] | 1:413 |
| Nalidixic acid (Nogram-Winthrop) | | 1:234 |

The compounds of general formula (I) can be administered in pharmaceutical compositions enterally and parenterally is solution, suspension or in solid form by admixture with a solid or liquid pharmaceutical diluent or carrier. Enteral and parenteral forms of administration can be of any conventional type, for example tablets, capsules, dragees, syrups, solutions, suspensions, drops, suppositories and the like. For this purpose, the active material is mixed with a solid or liquid carrier material and subsequently brought into the desired form. Examples of solid carrier materials include lactose, mannitol, starch, talc, methyl cellulose, silicic acid, calcium phosphate, magnesium stearate, agar-agar and gelatine to which, if desired can be added coloring materials and/or flavoring materials. Liquid carriers for injection solutions must be sterile and are preferably placed into ampoules. They are preferably administered in the form of tablets or dragees with a content of active material of 100-500 mg per tablet or dragee. The tablets can thereby contain further solid carrier materials, for example, starch, lactose, methyl cellulose, talc, highly dispersed silicic acid, high molecular weight fatty acids, magnesium stearate, gelatine, solid high moleculr weight polymers (for example polyethylene glycols) and, if desired, also flavoring and/or coloring agents.

Suspensions are preferably administered with a content of active materials of 20-100 mg/ml, using water as the suspension agent. For the stabilization of the suspensions, there can be added high molecular weight, water-soluble materials, for example, cellulose ethers or polyethylene oxide. Furthermore, there can also be added sweetening agents, flavoring agents, odiferous materials and/or coloring agents.

For injection solutions, the compounds of general formula (I) are preferably used in aqueous solution in amounts from 10–100 mg/dosage. Such injection solutions preferably also contain conventional additives, for example, stabilization agents, solubilizing agents, buffers and mannitol or sodium chloride in the amount necessary to produce an isotonic solution.

The active compounds of this invention will be administered to the afflicted subject according to methods known to the skilled artisan after being formulated as disclosed hereinabove or otherwise as also known in the art. Particularly in the application of the instant compounds to prevent or combat infections of the urinary tract, dosages of from 10 to 500 mg/kg of body weight may be desirably used, and these dosages are conveniently administered three times a day. However, different dosages may be appropriate in a given set of circumstances.

It will be understood that the foregoing specification and examples are illustrative but not limitative of the present invention inasmuch as other embodiments within the spirit and scope of the invention will suggest themselves to those skilled in the art.

What is claimed is:

1. Cyclopenteno-quinolone compound of the formula

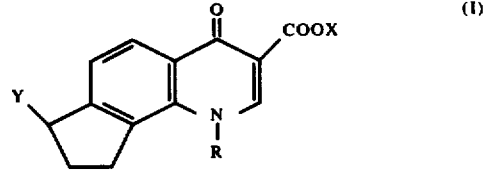

wherein
R is saturated or unsaturated aliphatic hydrocarbyl of up to 5 carbon atoms,
X is hydrogen or alkyl of up to 5 carbon atoms,
Y is azido, nitrile, amino, mono- or dialkylamino, mono- or dialkanoylamino, mono- or dialkylamino-methyleneamino, pyrrolidino or piperidino, of up to 5 carbon atoms per alkyl moiety,
and the pharmacologically compatible salts thereof.

2. Cyclopenteno-quinolone compound as claimed in claim 1, wherein R is alkyl of up to 3 carbon atoms.

3. Cyclopenteno-quinolone compound as claimed in claim 1, wherein X is hydrogen.

4. Cyclopenteno-quinolone compound as claimed in claim 1, wherein X is alkyl of up to 3 carbon atoms.

5. Cyclopenteno-quinolone compound as claimed in claim 1, wherein Y is azido.

6. Cyclopenteno-quinolone compound as claimed in claim 1, wherein Y is nitrile.

7. Cyclopenteno-quinolone compound as claimed in claim 1, wherein Y is amino, or mono- or dialkylamino of up to 3 carbon atoms in each alkyl moiety.

8. Cyclopenteno-quinolone compound as claimed in claim 1, wherein Y is mono- or dialkanoylamino wherein the alkanoyl moiety contains up to 3 carbon atoms.

9. Cyclopenteno-quinolone compound as claimed in claim 1, wherein Y is dialkylamino-methylene-amino wherein each alkyl moiety contains up to 3 carbon atoms.

10. Cyclopenteno-quinolone compound as claimed in claim 1, wherein Y is pyrrolidino.

11. Cyclopenteno-quinolone compound as claimed in claim 1, wherein Y is piperidino.

12. Cyclopenteno-quinolone compound as claimed in claim 1, wherein Y is unsubstituted amino.

13. Cyclopenteno-quinolone compound as claimed in claim 1, wherein said compound is 1-ethyl-3-carboxy-7-azido-1,4-dihydrocyclopenteno [1,2-h] quinol-4-one.

14. Pharmaceutical composition having bacteriostatic activity comprising a pharmaceutically acceptable carrier and, in effective amounts, at least one cyclopenteno-quinolone compound as claimed in claim 1.

15. Method of inducing a bacteriostatic effect in a subject which method comprises administering to such subject effective amounts of at least one cyclopenteno-quinolone compound as claimed in claim 1.

16. Method as claimed in claim 15 wherein such compound is applied in amounts of from 10 to 500 mg per dosage unit.

17. Method as claimed in claim 15 wherein said compound is selected from:
- 1-ethyl-3-carboxy-7-chloro-1,4-dihydrocyclopenteno [1,2-h] quinol-4-one,
- 1-ethyl-3-carboxy-7-azido-1,4-dihydrocyclopenteno [1,2-h] quinol-4-one, and
- 1-ethyl-3-carboxy-1,4-dihydro-7-methyl-sulphonyl-cyclopenteno [1,2-h] quinol-4-one.

* * * * *